(12) United States Patent
Araii

(10) Patent No.: US 6,969,348 B2
(45) Date of Patent: Nov. 29, 2005

(54) ENDOSCOPIC LIGHT SOURCE CONNECTOR

(75) Inventor: Kaoru Araii, Saitama (JP)

(73) Assignee: Fujinon Corporation, Saitama (JP)

( * ) Notice: Subject to any disclaimer, the term of this patent is extended or adjusted under 35 U.S.C. 154(b) by 179 days.

(21) Appl. No.: 10/437,066

(22) Filed: May 14, 2003

(65) Prior Publication Data

US 2003/0216618 A1 Nov. 20, 2003

(30) Foreign Application Priority Data

May 15, 2002 (JP) .............................. 2002-140292

(51) Int. Cl.[7] .............................. A61B 1/06; F21V 8/00
(52) U.S. Cl. ........................ 600/178; 362/581; 362/574
(58) Field of Search ................................ 600/132, 178; 362/574, 581, 449; 385/33, 34, 39, 52, 88

(56) References Cited

U.S. PATENT DOCUMENTS

| | | | | |
|---|---|---|---|---|
| 4,792,205 A | * | 12/1988 | Yin et al. ...................... | 385/80 |
| 4,913,523 A | * | 4/1990 | Yoshida et al. ................ | 385/15 |
| 5,146,523 A | * | 9/1992 | Maillot ........................ | 385/60 |
| 5,431,275 A | * | 7/1995 | Faulkner ...................... | 198/853 |
| 5,548,676 A | * | 8/1996 | Savage, Jr. ................... | 385/92 |
| 5,800,343 A | * | 9/1998 | Takeuchi et al. ............. | 600/132 |
| 6,135,626 A | * | 10/2000 | Glavind ....................... | 362/554 |
| 6,231,503 B1 | * | 5/2001 | Sugimoto et al. ........... | 600/178 |
| 6,689,050 B1 | * | 2/2004 | Beutter et al. .............. | 600/117 |

* cited by examiner

*Primary Examiner*—John P. Leubecker
(74) *Attorney, Agent, or Firm*—Oblon, Spivak, McClelland, Maier & Neustadt, P.C.

(57) ABSTRACT

In a socket portion of an endoscopic light source connector, a rod end holder is mounted on a riser plate within a housing of a light source for holding and supporting a fore end portion of a light guide rod of a light source connector, which has a proximal end portion of a light guide encased in a rigid pipe. The rod end holder is constituted by a fixed tubular casing which is mounted on the riser plate in an aligned position relative to an optical axis of illumination light path from a source lamp of the light source, and a slide member which is axially slidably fitted in the fixed tubular casing and internally provided with a light guide passage for passing illumination light from the source lamp. The light guide passage in the slide member is spread continuously or stepwise in the outward direction or toward the front side of the light source to permit connection of light guide rods of different diameters, and the slide member is constantly in an outward direction or in a direction inverse to the direction of insertion of a light guide rod.

6 Claims, 5 Drawing Sheets

F I G. 1
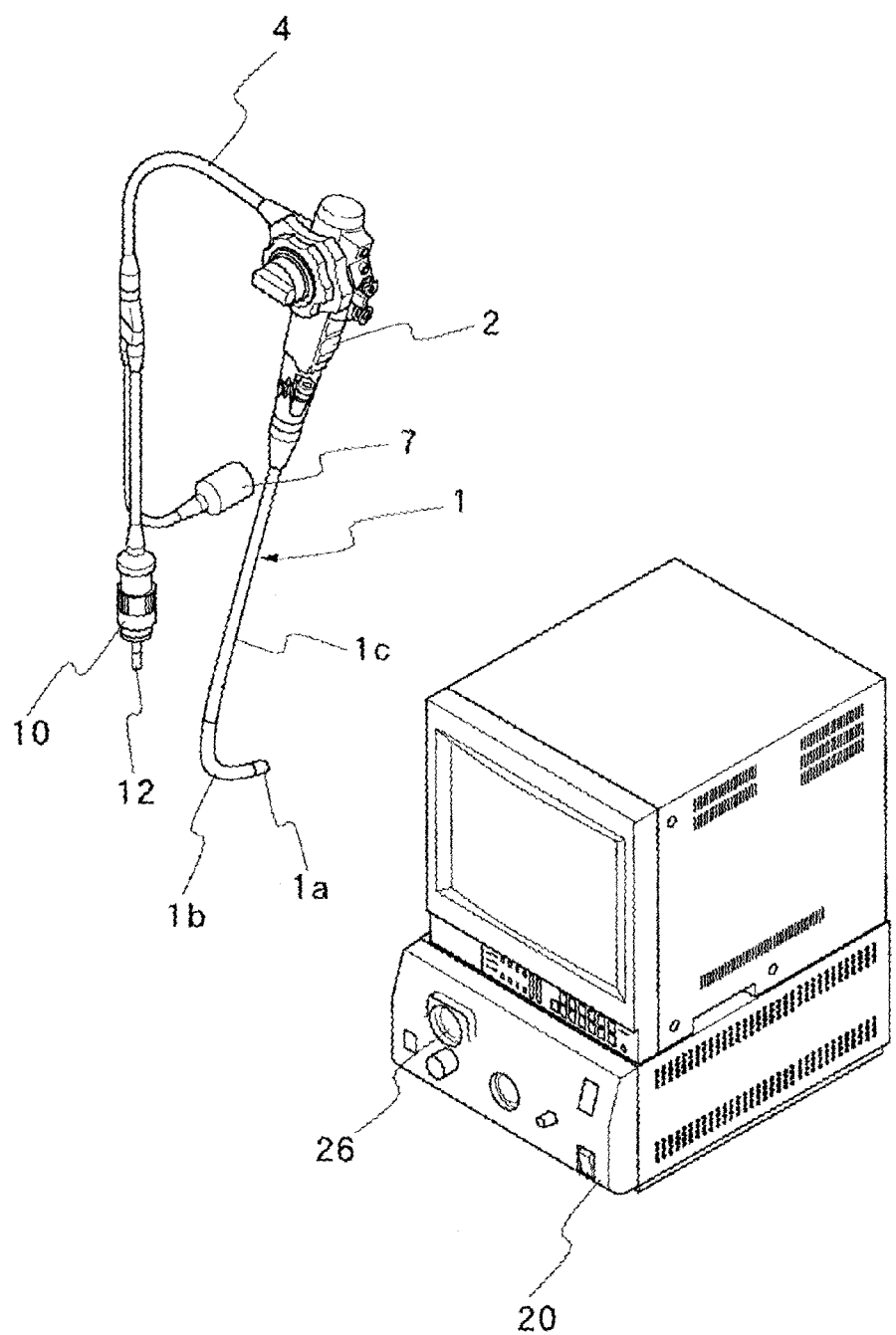

F I G . 3
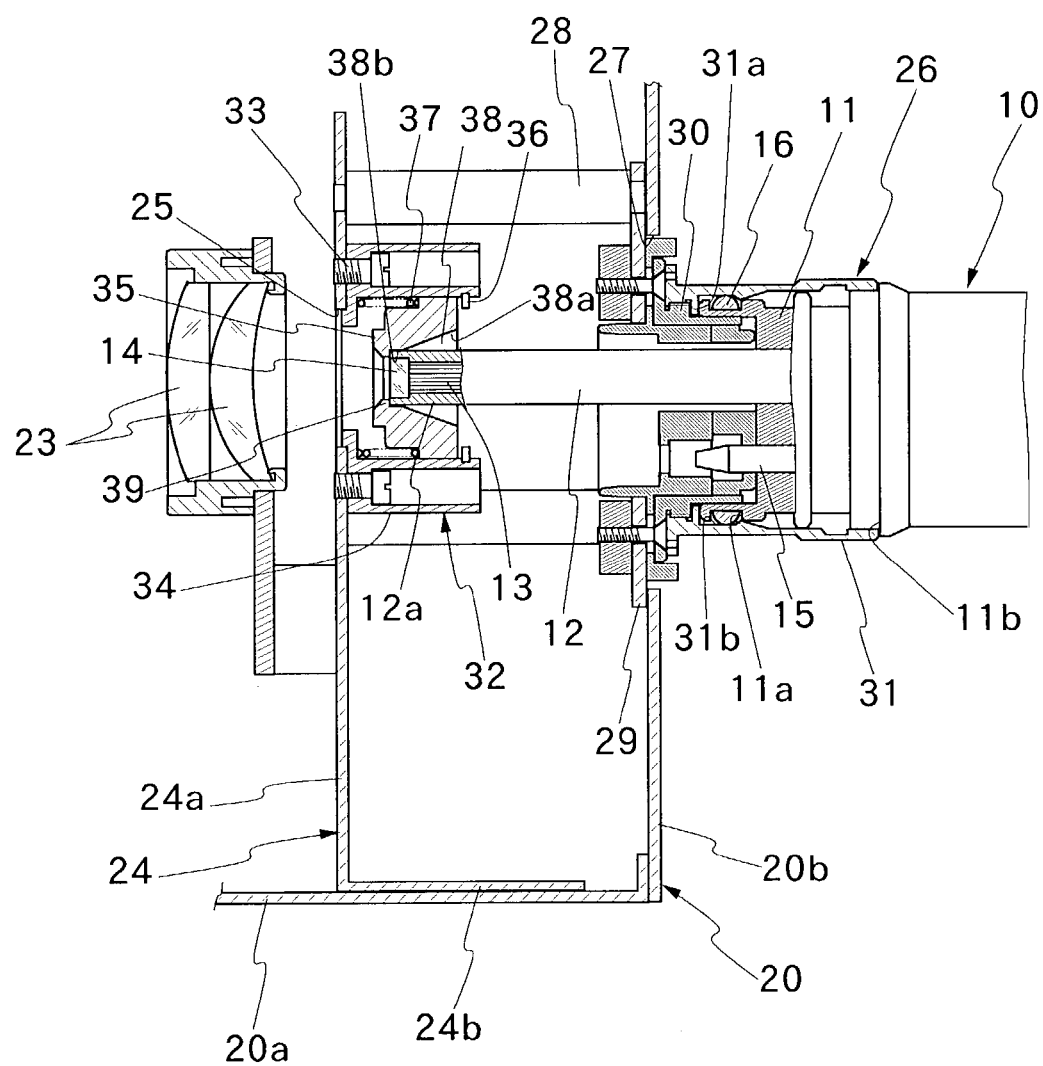

F I G. 4
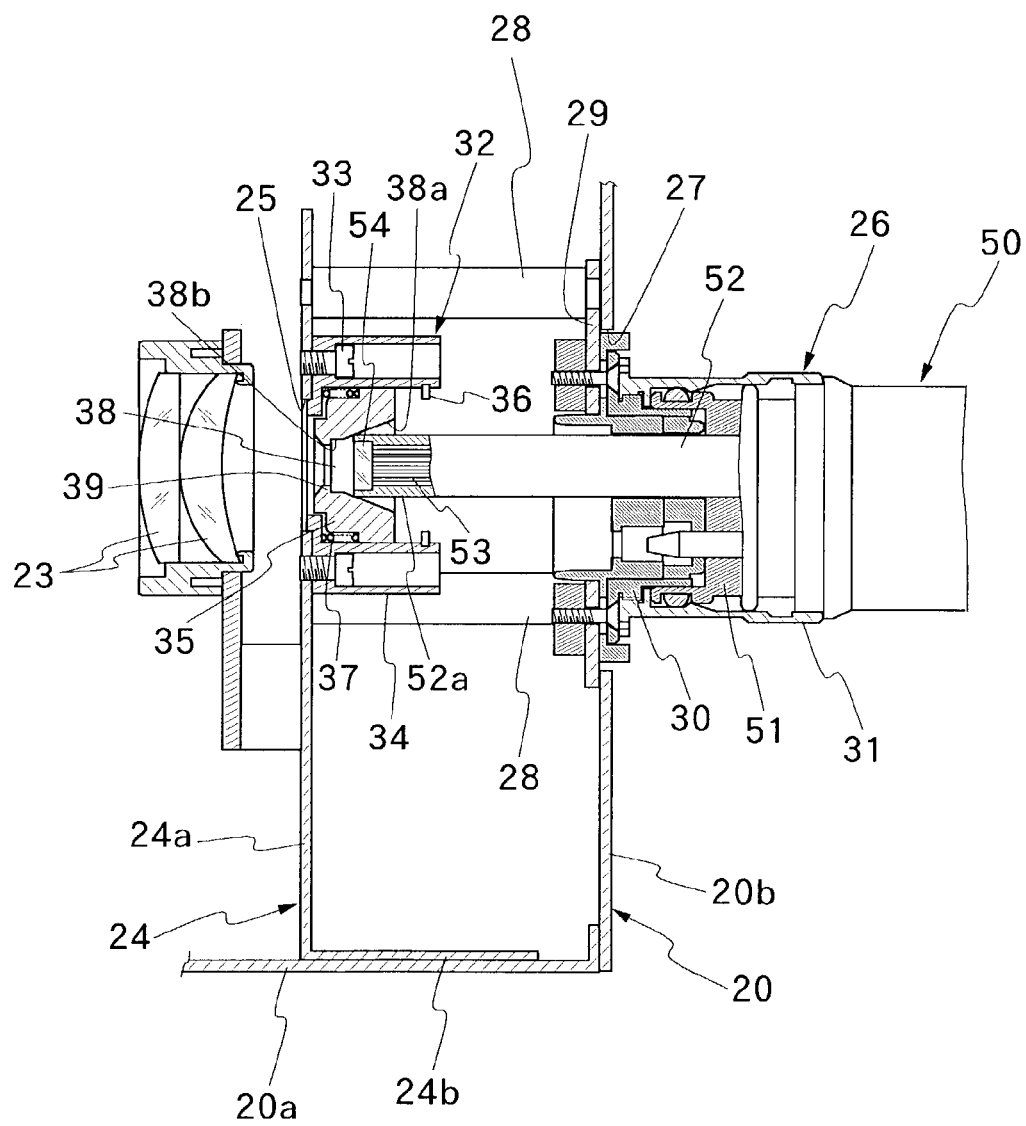

ENDOSCOPIC LIGHT SOURCE CONNECTOR

BACKGROUND OF THE INVENTION

1. Field of the Art

This invention relates to construction of an endoscopic light source connector for connecting a light guide of an endoscope to a light source, to transmit illumination light to a subject under endoscopic observation, the light source connector having a plug portion which is provided on the side of the endoscopic light guide and a socket portion which is provided on the side of a casing of the light source which houses a source lamp.

2. Prior Art

Endoscopes which are in use in medical fields are generally constituted by an insertion instrument which is extended out on the front side of a manipulating head assembly, and a universal cable which is led out on the rear side of the manipulating head assembly in the opposite direction away from the insertion instrument. The universal cable is provided with a light source connector at its proximal end to be disconnectibly connected to an illumination light source device having an illumination lamp housed in a casing. For this purpose, a socket portion is provided on the side of the light source casing.

In use, usually an endoscope of a suitable construction is selected depending upon the operator's taste or familiarity. Alternatively, an endoscope of a particular type is used depending upon the purpose of use or depending upon the nature of an endoscopic examination to be conducted. On the other hand, a light source to be installed in an endoscopic examination room is desirably arranged to permit connection of endoscopes of different types. One and single light source can be used for various types of endoscopes if plug portions on the respective endoscopes are constructed to common dimensional specifications. For instance, in the case of Japanese Laid-Open Patent Application S58-152532, light source connectors of different constructions are connected to a socket portion of one light source by the use of an adaptor.

In order to ensure smooth painless introduction into a body cavity, it is a paramount requisite for an endoscopic insertion instrument to be as small as possible in diameter or thickness. The same applies to a light guide to be threaded through the insertion instrument. In order to transmit a sufficient amount of light through a narrow light guide, it is necessary for a light source to employ a source lamp which can emit a large quantity of light, for example, a high intensity lamp like a xenon lamp. However, use of a xenon lamp involves a number of problems. For example, it requires an exclusive starting device, in addition to the difficulties that it is costly and necessitate to provide a light source which is larger in construction as a whole. For these reasons, there has been a trend toward employing a simpler halogen lamp as an endoscopic light source. As compared with a xenon lamp, a halogen lamp is lower in light intensity. Therefore, in the case of a light source with a low intensity lamp, it becomes necessary to enhance light condensing efficiency by using a light guide of a larger diameter.

As described above, high intensity lamps as well as low intensity lamps have been employed as a source lamp in various endoscopic light sources. In this regard, it is not desirable to connect a narrow light guide to a light source with a low intensity lamp because it will result in an insufficient illumination light level. In this regard, it is possible to connect a thick light guide to a high intensity lamp. However, transmission of illumination light in an excessively large volume can result in halation of endoscopic images because a solid-state image sensor device is likely to be saturated with increased light reflections off intracavitary walls, in addition to a problem of increased heat radiation toward the intracavitary wall. These problems can be eliminated to a certain degree by lowering the light intensity or by using a filter or the like. Accordingly, it is not impossible to connect an endoscope with a light guide of a relatively large diameter to a light source having a high intensity lamp.

The plug portion on the side of the light guide to be disconnectibly connected to a socket portion on a light source casing is arranged into a rod-like shape which is generally referred to as "light guide rod." In some cases, for the purpose of facilitating connections and disconnections, the light guide rod is arranged to be lightly connected with the socket portion at the sacrifice of the stability of the light guide rod in the connected state. Besides, usually a light guide rod is projected out of a light source connector casing, and the light guide rod is arranged to protrude largely into a light source through a coupling portion in a socket portion. Therefore, there are possibilities of the plugged end of the light guide rod being put in quaking movements when the universal cable is pulled taut or when the casing of the light source is vibrated.

As the light source connector is plugged into the socket, the light guide rod is brought into alignment with the optical axis of an illumination light path from the source lamp. However, if the light guide rod is put in a vibrating movement, flickering of illumination light or variations in illumination light level occur due to repeated deviations of the light guide rod from the optical axis of the light source. Therefore, it is desirable to provide on the side of the light source a centering mechanism with a rod end holder for fixedly holding a tip end portion of the light guide rod in an aligned position, for example, as disclosed in Japanese Laid-Open Utility Model Application H3-26491.

Thick and narrow light guide rods conspicuously differ from each other in diameter. Therefore, in making it possible to connect two different types of light guide rods to one common light source, it becomes necessary for the light source to employ a centering mechanism with a rod end holder which is capable of holding both thick and narrow light guide rods in an aligned center position despite differences in diameter.

SUMMARY OF THE INVENTION

In view of the foregoing situations, it is an object of the present invention to provide an endoscopic light source connector which makes it possible to connect both thick and narrow endoscopic light guide rods of different diameters commonly to one and same light source.

It is another object of the present invention to provide an endoscopic light source connector which makes it possible to plug endoscopic light guide rods of different diameters into a common light source, holding the light guide rods securely in an aligned center position relative to a path of illumination light from the light source despite differences in diameter to prevent dipping or flickering of illumination light.

In accordance with the present invention, in order to achieve the above-stated objectives, there is provided an endoscopic light source connector for connecting an endoscopic light guide in the form of a bundle of fiber optics detachably to a light source, the light guide having a light receiving end portion thereof encased in a rigid pipe and projected from a distal end of a connector casing over a predetermined length to form a light guide rod to be plugged into a socket portion of the light source, characterized in that the socket portion on the side of the light source comprises: a rod end holder fixedly mounted on a riser plate within a light source casing for holding a fore end portion of the guide rod, the rod end holder being composed of a fixed tubular casing fixedly mounted on the riser plate in alignment with optical axis of an illumination light path from a source lamp of the light source, and a slide member axially slidably fitted in the tubular casing and internally defining a light guide passage for passing illumination light from the source lamp; the light guide passage in the slide member being in the form of an outwardly spread light guide passage having an inside diameter increased continuously or stepwise in an outward direction toward front side of the light source casing to permit connection thereto of various light guide rods of different diameters, and the slide member being constantly urged in an outward direction or in a direction toward a plugged light guide rod by a biasing means.

The fore distal end of the light guide rod which is largely projected from a casing of the light source connector is supported on the riser plate within the fixed tubular casing of the rod end holder which is located in alignment with optical axis of illumination light path from the source lamp. However, in order to support light guide rods of different outside diameters, the fore distal end portion of a light guide rod is brought into fitting engagement not directly with the fixed tubular casing but with a slide member which is axially slidably fitted in the fixed tubular casing of the rod end holder. Therefore, an internal light guide passage within the slide member is spread into a larger diameter from an inner end or from a halfway point toward its outer end or in an opposite direction relative to a light guide rod plugging direction. The light guide passage within the slide member may be spread into a larger diameter either continuously or stepwise. Preferably, the outwardly spread light guide passage is constituted by a conical inner peripheral surface of the slide member. The conical inner peripheral surface may be provided along the entire length of the light guide passage, but it is preferable to provide a cylindrical portion of a certain length on the inner side of the narrowest inner end of the conically spread portion of the light guide passage.

In a case where the internal light guide passage of the slide member is constituted by a conically spread portion and a cylindrical portion, it is arranged such that a fore end portion of a light guide rod which is smallest in diameter fits in the cylindrical portion of the light guide passage. A fore distal end of a larger light guide is abutted against the conical inner peripheral surface and retained in pressed contact with the latter by a biasing means. Preferably, an inwardly projecting annular ridge is provided on the inner side of the cylindrical 1s portion of the light guide passage which is arranged to be held in abutting engagement with a fore end of a rigid pipe of the narrowest light guide rod and at the same time to serve as a stop member which limits the amount of input illumination light to be shed on a light incident end face of a thick light guide rod which is abutted against the conical inner peripheral surface of the slide member.

In case the source lamp of the light source is a high intensity type, illumination light is shed substantially on the entire light incident end face of the narrowest light guide rod. Accordingly, the thicker light guide rod which is abutted against the conical inner peripheral surface of the slide member can be of the sort which is originally intended for use with a low intensity light source. In this instance, the light guide passage to the light incident end face of the thick light guide rod is restricted by the above-mentioned annular ridge. In this case, however, as compared center regions, illumination light is shed in a conspicuously reduced amount in outer peripheral regions of the light incident end face of the light guide rod. In this regard, in order to let the light guide transfer illumination light uniformly across the sectional area of its bundle of fiber optics, it is preferable to shuffle the positions of fiber optics randomly toward its light emitting end.

Preferably, a condensing lens is mounted on the riser plate of the socket portion thereby to condense the illumination light from the source lamp and to improve all the more the alignment of the light guide with the illumination light path. From the standpoint of structural strength, the riser plate member is preferably constituted by a metal plate. In the case of a metal plate, the slide member is formed of an electrically insulating material.

The above and other objects, features and advantages of the present invention will become apparent from the following particular description of the invention, taken in conjunction with the accompanying drawings which show by way of example some preferred embodiments of the invention. Needless to say, the present invention should not be construed as being limited to particular forms shown in the drawings.

BRIEF DESCRIPTION OF THE DRAWINGS

In the accompanying drawings:

FIG. 1 is a schematic illustration showing general layout of an endoscope;

FIG. 3 is a schematic sectional view showing a light guide rod of an endoscope, which has been plugged into a socket portion of a light source;

FIG. 4 is a schematic sectional view showing a light guide rod of a larger diameter plugged into the socket portion of the light source.

DESCRIPTION OF PREFERRED EMBODIMENTS

Figure 2:
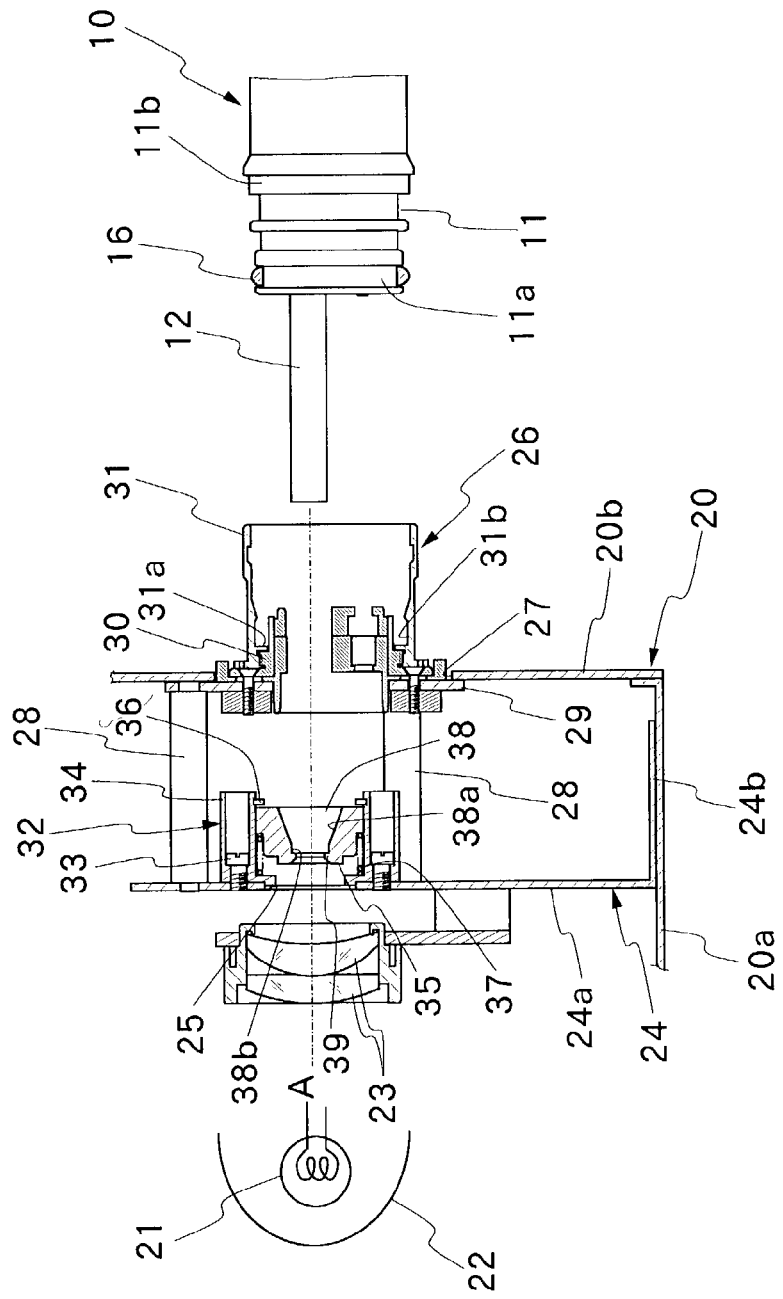
FIG. 2 is a schematic outer view of an embodiment of the endoscopic light source connector according to the present invention, showing a plug portion of the connector in a separated state from a socket portion on a casing of a light source shown in vertical section.

Hereafter, the present invention is described more particularly by way of its preferred embodiments with reference to the accompanying drawings.

Illustrated schematically in FIG. 1 is the general layout of one typical endoscope which has been in use for medical purposes. In this figure, indicated at 1 is an insertion instrument to be introduced into a body cavity of patient. The insertion instrument 1 of the endoscope is composed of a rigid tip end section 1a which supports thereon an endoscopic observation mechanism including an illumination window or windows and an observation window, an angle section 1b which is connected to the proximal end of the rigid tip end section 1a and angularly bendable by remote control to turn the rigid tip end section 1b into a desired direction, and an elongated flexible body portion 1c which is flexibly bendable in arbitrary directions along a path of insertion. The proximal base end of the flexible body portion 1c is connected to a manipulating head assembly 2 to be gripped by an operator for manipulating the insertion instrument 1. A manual operating knob or knobs are provided on the manipulating head assembly 2 along with an air/water feed valve etc.

The endoscopic insertion instrument 1 is usually introduced into a dark body cavity and therefore needs to illuminate an intracavitary site to be observed or examined. For this purpose, a light emitting end of a light guide is extended to and disposed in an illumination window which is provided on the rigid tip end section 1a. The opposite light input end of the light guide is disposed in a path of illumination light from a source lamp which is housed in an endoscopic light source unit 20. Thus, illumination light from the source lamp is transferred through the light guide and delivered to the illumination window to illuminate an intracavitary site forward of the observation window of the endoscope. To this end, the light guide is encased in the universal cable 4 which is extended out from the manipulating head assembly 4.

Provided at the proximal end of the universal cable 4 is a light source connector 10 which is detachably connectible to the light source 20. In this instance, the afore-mentioned light guide is constituted by a bundle of extremely fine fiber optics and flexible in bending directions. A proximal end portion of the light guide is encased in a rigid pipe which is projected from a casing 11 of the light source connector 10 to provide a light guide rod 12.

In the case of an electronic endoscope employing a solid-state image sensor device inside the observation window, a signal cable from the solid-state image sensor device is connected to a video signal processor. This video signal cable is passed also through the above-mentioned universal cable and separated from the light guide at a halfway point and detachably connected to the video signal processor by means of a video cable connector 7. The illumination light source and the video signal processor are provided either as separate units or as one complex unit.

Shown schematically in FIG. 2 is the light source connector 10 on the side of the endoscope, to be plugged into a socket portion on the side of the light source 20, and shown in an enlarged sectional view in FIG. 3 is the light source connector 10 which has been plugged into the light source 20. As clear from these figures, the light guide rod 12 is constituted by a bundle of fiber optics in a proximal end portion of the light guide 13, which is encased in a rigid pipe 12a. A light incident end face at the proximal end of the light guide 13 is faced toward cover glass 14 which is fitted in the distal end of the rigid pipe 12a. Indicated at 15 is a pipe which is projected from the distal end of the connector casing 11 and to which an air/water feed tube is detachably connectible.

A source lamp 21 is mounted internally of a casing of the light source 20. Illumination light from the source lamp 21 is condensed toward a predetermined point by means of first and second condensing members which are in the form of a concave mirror 22 and a condensing lens 23, respectively. In FIG. 2, the letter A indicates the optical axis of a light path. Although omitted in the drawings, a stop member is located in the light path between the source lamp 21 and the condensing lens 23.

The light source 20 is provided with a casing which is formed in a box-like shape including a base 20a, and a majority of component parts of the light source 20 are mounted on the base 20a including the source lamp 21, concave mirror 22 and condensing lens 23. In the drawings, indicated at 24 is a riser plate which supports a lens tube of the condensing lens 23 thereon. The riser plate 24 is constituted by an L-shaped metal strip with an aperture 25 opened in its vertical plate portion 24a. The aperture 25 is formed in a predetermined diameter to provide a light guide path including the optical axis A of illumination light. A bent lower end portion 24b is abutted against and securely fixed to the base 20a by screws or other suitable fixation means.

A socket portion 26 which receives the light guide rod 12 of the light source connector 10 is supported on the vertical plate portion 24a. A front panel 20b of the light source casing is provided with an opening 27 to receive the socket assembly 26 therein. A plural number of horizontal posts 28 are fixedly provided on the riser plate 24, and the socket portion 26 is supported on an annular support plate 29 which is attached to fore ends of the horizontal posts 28.

The socket portion 26 is constituted by an assembly of an inner tube 30 and an outer tube 31 which are each formed of an electrically insulating material. The outer tube 31 is provided with an inward flange portion 31a around the inner periphery of its fore end portion, and an annular stopper groove 31b is formed at a position on the outer side of the inward flange portion 31a. When plugged in, an annular ring-like portion at the fore end of the casing 11 of the light source connector 10 is inserted between the inner and outer tubes 30 and 31 of the socket portion 26. An annular circumferential groove 11a is formed around the outer periphery of the connector casing 11, and a resilient ring 16 is fitted in the annular circumferential groove 11a. Upon plugging the light source connector 10 into the socket portion 26, the fore end portion of the connector casing 11 is abutted against the inward flange portion 31a of the outer tube 31, and the resilient ring 16 is brought into engagement in the annular groove 31b of the outer tube 31. At the same time, a fore end portion of the outer tube 31 is brought into abutting engagement with a stepped portion 11b which is provided around the circumference of the connector casing 11.

Further, indicated at 32 in the drawings is a rod end holder which serves to support a fore distal end portion of the light guide rod 11. The rod end holder 32 is composed of a fixed tubular casing 34 which is securely fixed to the riser plate 24 by means of screws 33, and a slide member 35 which is slidably received in the fixed tubular casing 34. The fixed tubular casing 34 is fixed to the riser plate 24 in such a way as to circumvent the aperture 25 and its axis is located in alignment with the optical axis A. The slide member 35 is formed of an electrically insulating material, and slidable in axial directions within the fixed tubular casing 34. Namely, the slide member 35 is immovable in directions other than axial directions. A stopper ring 36 is planted on the inner periphery of the fixed tubular casing 34 at a position close to its fore end, which is located away from the riser plate 24, and a spring 37 is interposed as a biasing means between the fixed tubular casing 34 and the slide member 35 thereby to urge the slide member 35 toward and into abutting engagement with the stopper ring 36.

The slide member 35 is internally formed with a light guide passage 38. This light guide passage 38 is formed axially through the slide member 35 in alignment with the optical axis A, and in a conical shape defined by a conical inner peripheral wall portion 38a converging continuously in the inward direction or in the light guide rod inserting direction as far as a short cylindrical portion 38b, which is provided at the inner end of the light guide passage 38.

Accordingly, when seen from the side of the source lamp 21, the conical inner peripheral wall portion 38a of the light guide passage 38 is a diverging passage portion having a diameter which is continuously increased in the forward or outward direction from the cylindrical portion 38b toward its fore end. Further, the slide member 35 is provided with an inwardly projecting annular ridge 39 on its inner periphery at a position corresponding to the foremost position which will be taken by the light guide rod 12 when plugged into the socket portion 26. In this instance, the cylindrical portion 38b of the light guide path 38 is formed to have an inside diameter which is substantially same as the outside diameter of the light guide rod 12. Therefore, when the light guide rod 12 is plugged into the socket portion 26, a fore end portion of the light guide rod 12 just fits in the cylindrical portion 38b of the slide member. At the same time, the fore end face of the rigid pipe 12a of the light guide rod 12 is abutted against the annular ridge 39 on the inner periphery of the slide member 35.

With the arrangements as described above, upon plugging the light guide rod of the light source connector into the socket portion 26 of the light source 20 and turning on the source lamp 21 as shown in FIG. 2, a necessary amount of illumination light is taken into the light guide 13 within the light guide rod 12 and projected toward an intracavitary site under observation through the illumination window on the rigid tip end section 1a of the endoscopic insertion instrument 1. In this way, an intracavitary site of interest is illuminated with illumination light to permit precise and accurate endoscopic observation or examination through the observation window.

Upon plugging the light source connector 10 into the socket portion 26, a fore end portion of the casing 11 of the light source connector 10 is inserted between the inner and outer tubes 30 and 31 of the socket portion 26, and at the same time the resilient ring 16 in the annular circumferential groove 11a on the casing 11 is engaged in the annular groove on the inner periphery of the outer tube 31. As a consequence, the light source connector 10 is stably maintained in the connected state, and would not drop off even if some external forces are applied thereto. Further, in the connected state, the fore end of the light guide rod 12 of the connector 10 is held in the cylindrical portion 38b of the slide member 35 of the rod end holder 32, which is fixed on the riser plate 24, while the end face of the rigid pipe 12a is abutted against the annular ridge portion 39 which is formed around the inner end of the cylindrical portion 38b of the slide member 38. At this time, the light source connector 10 is brought into abutting engagement with the inner and outer tubes 30 and 31 of the slide member 35 of the socket portion 26, which are formed of an electrically insulating material. Therefore, even if the rigid pipe 12a of the light source connector 10 is formed of a metallic material, the light source connector 10 can be maintained in an electrically insulated state from the light source 20.

While the endoscope is manipulated by an operator, it is usually the case that various forces are applied on the universal cable. The light source connector 10 is also affected by the external disturbing forces, and as a result coupling portions of the light source connector 10 with the light source 20 are put under influences of vibrations from the ambience. Since the light guide rod 12 is projected from the casing 11 of the light source connector 10, it is often found difficult to stop the fore end of the light guide rod 12 from vibrating under the influence of the above-mentioned externally applied forces. However, according to the present invention, the fore end of the light guide rod 12 is gripped in the cylindrical portion 38b of the slide member 35, which is supported on the riser plate 24 through the fixed tube member 34. Likewise, the condensing lens 23 which converges the illumination light from the source lamp 21 is also supported on the riser plate 24.

Accordingly, an external force of a certain magnitude is applied on the coupled portions of the light source connector 10 and the socket portion 26, at least the fore end of the light guide rod 12 is maintained in alignment with the optical axis A of the condensing lens 23. Consequently, the light incident end face of the light guide 13 is constantly maintained in an aligned state relative to the optical axis A of the condensing lens 23 in such a way as to prevent deviations or inclinations of the optical axis which would result in variations in illumination light intensity or flickering of illumination light.

In case a light source 20 having a high intensity lamp 21 like a xenon lamp in its lamp house, it is normally used for light source connectors with a light guide rod of a relatively small diameter as compared with light source connectors which are intended for use with other light sources employing a low intensity lamp like a halogen lamp. Accordingly, the light guide rod 12 is a narrow type which is reduced in diameter. More specifically, the light guide rod 12 of the light source connector 10 is shown as a narrowest type.

In this instance, with regard to the light source connectors which are originally intended for use with other light sources because of differences in diameter of the light guide rod, there is no need for changing the construction of the light source connectors or connector casings for connection to the socket portion. In this regard, from the standpoint of making it possible to use common component parts or modules, it is rather desirable to employ the same construction not only for the socket portion on the light source 20 but also for socket portions on other light sources, employing the same construction for the casing of each light source connector as well.

However, in the case of light source connectors which are adapted to be connected to other light sources with a low intensity lamp, the light guide rod is thicker and the light guide has a larger light incident end face. Therefore, it is normally difficult to connect the light source connector to the light source 20 because of the provision of the rod end holder 32 and because of the difficulty which one may encounter in controlling a large volume of illumination light from the high intensity lamp 21 to a sufficient degree simply by reducing the light volume by means of a stop member or the like.

These difficulties or problems are solved by the provision of the rod end holder 32 having the slide member 35 axially slidably fitted in the fixed tubular casing 34. Namely, FIG. 4 shows a light source connector 51 which is same as the light source connector 10 in construction and shape. In this case, however, a light guide rod 52 which is projected from its casing 51 is thicker than the above-described light guide rod 12. The light guide rod 52 is comprised of a light guide 53 which is encased in a rigid pipe 52a. A light receiving end of the light guide 53 is disposed face to face with cover glass 54. In order to take in illumination light efficiently from a low intensity lamp and transfer the illumination light to the light emitting end without losses, the number of fiber optics in the light guide 53 is increased to make its light receiving surface area broader, namely, to secure a larger numerical aperture (NA) for the light guide rod. In this case, the outside diameter of the rigid pipe 52a of the light guide rod 52 is increased accordingly.

As the light source connector 50 is connected to the light source 20, the light guide rod 52 is brought into abutting engagement with the conical wall portion 38a of the slide member 35 of the rod end holder 32. As soon as the light source connector 50 is plugged into a predetermined position within the socket portion 26, slide member 35 is pushed inward by the fore end of the light guide rod 52 against the biasing action of the spring 37. Accordingly, the fore end of the light guide rod 52 is pressed against the conical wall portion 38a of the slide member 35 which is under the influence of the biasing action of the spring 37. Since in this manner the light guide rod 52 is pressed against the conical wall portion 38a of the slide member 35 in the light guide path 38, it is automatically urged into and retained in a center position within the light guide path 38. Besides, the slide member 35 is retained in the fixed tubular casing 34 which is fixedly mounted on the riser plate 24, in alignment with the condensing lens 23 which is also fixedly mounted on the riser plate 24. Therefore, the light guide 53 in the light guide rod 52 is retained precisely in alignment with optical axis of the illumination light path.

Figure 5:
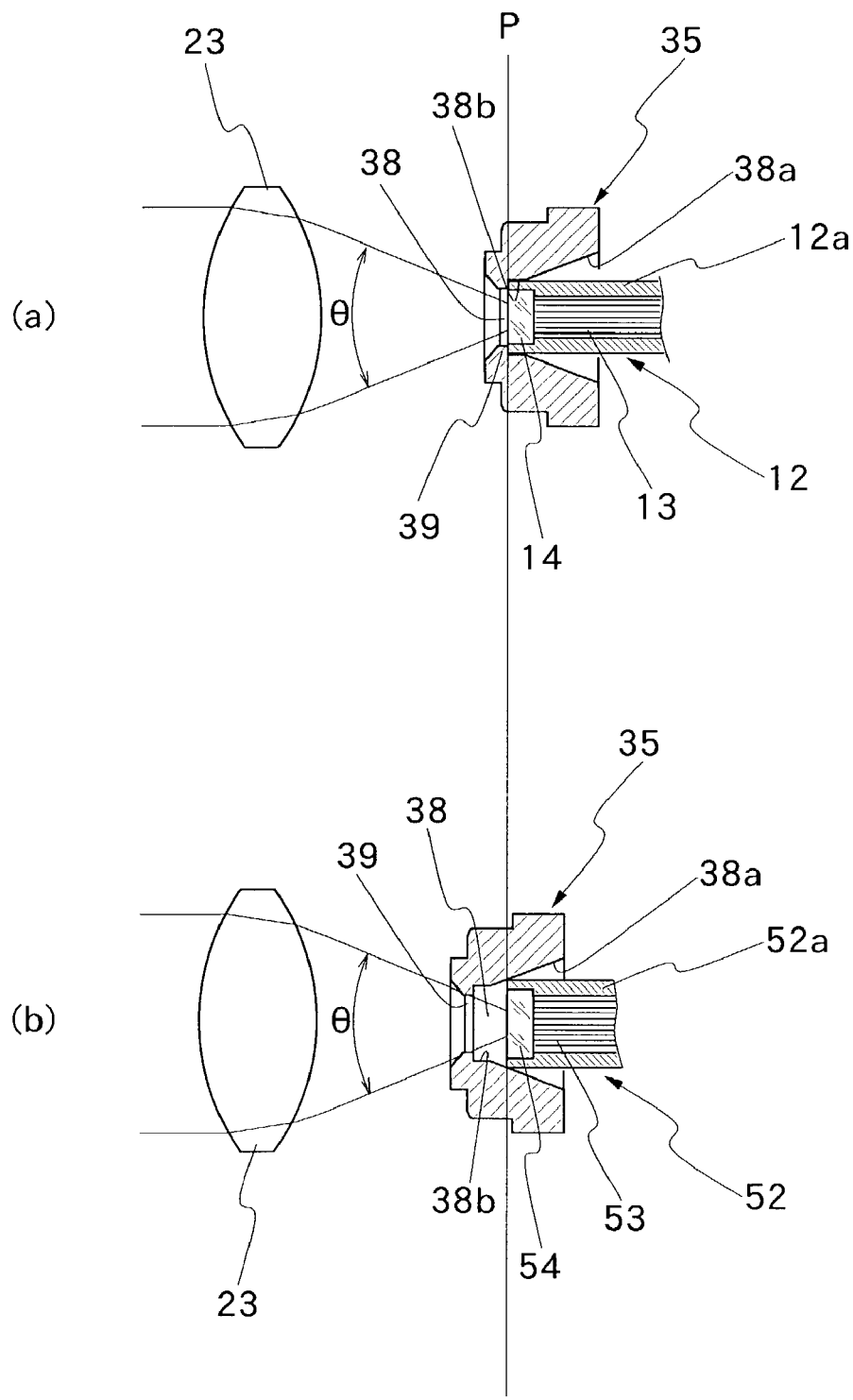
FIG. 5 is a schematic illustration explanatory of quantities of input illumination light incident on the narrow and thick light guide rods of FIGS. 3 and 4.

Illumination light coming through the light guide path 38 is shed on the light guide 53. In this instance, the light guide path 38 has a smallest aperture size at the annular ridge 39 which is provided in its inner end portion on the side of the condensing lens 23. Accordingly, when the light source connector is plugged into the light source 20, the annular ridge portion 39 functions as a stop member for the light path. Therefore, the amount of input light to the light guide 13 of the light source connector 10, which is shown at (a) of FIG. 5, can be substantially equalized with that of input light to the light guide 53 of the light source connector 50 which is shown at (b) of FIG. 5.

More particularly, as long as the light guide rods 12 and 52 are same with each other in length, fore distal ends of these light guide rods 15 and 52 are located at the same position P in the path of illumination light. In this case, if illumination light is shed on the light-receiving face of the light guide 13 of the light guide rod 12 at an angle of incidence θ, the annular ridge 39 does not function as a stop because the aperture size of the annular ridge 39 is appreciably larger than the light incident end face of the light guide 13. When the light guide rod 52 is plugged in, the light incident end face of the light guide 53 in the light guide rod 52 comes to the same position as that of the light guide 12. However, at this time the slide member 35 is pushed back to a position which is at a shorter distance from the condensing lens 23. Therefore, this time the aperture of the annular ridge portion 39 functions as a stop limiting the input light to the light incident face of the light guide 53 to the angle of incidence θ. That is to say, input illumination light is shed only in a limited surface range on the entire light incident face of the light guide 53. Therefore, despite the difference in breadth of the light incident end face, the same amount of input light can be fed to the light guides 13 and 53.

It follows that, even if the light source connector 50 with the thick light guide 53 is plugged into and connected to the high intensity light source 20, there is no possibility of illumination light being transmitted to the light guide 53 in an excessive amount. This means that an operator can obtain clear images of an intracavitary site of interest while preventing excessive heat radiation on intracavitary walls to ensure smooth and safe endoscopic examinations.

In addition, no matter whether the light guide 13 or the light guide 53 is connected, illumination light is constantly fed to the same position and at the same angle of incidence. Therefore, despite the difference in the size of the light incident end face of the light guide, the same control of the input light is feasible even in a case where the light source is provided with the so-called automatic gain control mechanism (AGC) to control a variable stop, which is provided in the illumination light path between the source lamp 21 and the condensing lens 23, in relation with gains in light level received by the solid-state image sensor device of the endoscope.

By the way, illumination light is shed only on a limited area of the light incident end face of the light guide 53. Therefore, if illumination light is transmitted through fiber optics in a limited cross-sectional area of the light guide 53, it is emitted from the light emitting end of the light guide in an uneven pattern which is bright in a center area but dark in peripheral areas. However, the illumination light can be emitted uniformly across the light emitting end of the light guide 53 by randomly shuffling the positions of the fiber optics from the light receiving end toward the light emitting end of the light guide. As a result, an intracavitary portion under observation is uniformly illuminated with the illumination light from the light guide.

What is claimed is:

1. An endoscopic light source connector for connecting an endoscopic light guide in the form of a bundle of fiber optics detachably to a light source, said light guide having a light receiving end portion thereof encased in a rigid pipe and projected from a distal end of a connector casing over a predetermined length to form a light guide rod to be plugged into a socket portion of said light source, characterized in that said socket portion on the side of said light source comprises:

a rod end holder fixedly mounted on a riser plate within a light source casing for holding a fore end portion of said guide rod, said rod end holder being composed of a fixed tubular casing fixedly mounted on said riser plate in alignment with an optical axis of an illumination light path from a source lamp of said light source, and a slide member axially slidably fitted in said tubular casing and internally defining a light guide passage for passing illumination light from said source lamp;

said light guide passage in said slide member being in the form of an outwardly spread light guide passage having a conical passage portion formed by a conical inner peripheral wall portion over a predetermined axial length from an outer end of said outwardly spread light guide passage, a cylindrical passage portion formed continuously over a predetermined length from a narrowest inner end of said conical passage portion; and said slide member being constantly urged in an outward direction or in a direction toward a plugged light guide rod by a biasing means, whereby said cylindrical passage portion being adapted to receive the narrowest light guide rod and light guide rods of larger diameters being received on a conical wall surface of said conical passage portion and being held said light guide rods in pressed contact with said conical wall surface by said biasing means.

2. An endoscopic light source connector as defined in 1, further comprising an inwardly projecting annular ridge portion formed on the inner side of said cylindrical passage portion of said light guide passage in said slide member for abutting engagement with an end face of a rigid pipe of a narrowest one of light guide rods to be connected with said light source, said annular ridge portion serving as a stop member for limiting the amount of input light to a light guide rod of a larger diameter in abutting engagement with said conical wall surface of said slide member.

3. An endoscopic light source connector as defined in claim 2, wherein said source lamp of said light source is a high intensity lamp, illumination light from said high intensity lamp being shed substantially on an entire area of a light incident end face of a light guide in case of said narrowest light guide rod, but said annular ridge acting as a stop letting illumination light from said high intensity lamp fall on a limited area on a light incident end face of a light guide in case of a light guide rod of a larger diameter originally adapted to transfer illumination light from a low intensity lamp.

4. An endoscopic light source connector as defined in claim 3, wherein positions of fiber optics at least in a light guide in said light guide rod of a larger diameter are randomly shuffled toward a light emitting end of said light guide.

5. An endoscopic light source connector as defined in claim 1, further comprising a condensing lens mounted on said riser plate for condensing illumination light from said source lamp toward said slide member.

6. An endoscopic light source connector as defined in claim 1, wherein said riser plate is constituted by a metal plate and said slide member is formed of an electrically insulating material.

* * * * *